US006427698B1

(12) United States Patent
Yoon

(10) Patent No.: US 6,427,698 B1
(45) Date of Patent: Aug. 6, 2002

(54) INNOMINATE OSTEOTOMY

(76) Inventor: Taek-Rim Yoon, 104-402 Keumho Apt., #1130 Poongam-Dong, Seo-Gu, Kwangju 502-156 (KR)

( * ) Notice: Subject to any disclaimer, the term of this patent is extended or adjusted under 35 U.S.C. 154(b) by 0 days.

(21) Appl. No.: 09/764,173

(22) Filed: Jan. 17, 2001

(51) Int. Cl.[7] .............................................. A61B 19/00
(52) U.S. Cl. ...................................................... 128/898
(58) Field of Search ............................ 128/898; 606/79

(56) References Cited

U.S. PATENT DOCUMENTS

| | | | | |
|---|---|---|---|---|
| 5,035,698 A | * | 7/1991 | Comparetto | 606/79 |
| 5,263,498 A | * | 11/1993 | Caspari et al. | 128/898 |
| 5,275,601 A | * | 1/1994 | Gogolewski et al. | 606/69 |
| 5,423,822 A | * | 6/1995 | Hershberger et al. | 606/79 |
| 6,059,831 A | * | 5/2000 | Braslow et al. | 128/898 |

OTHER PUBLICATIONS

Robert B. Salter, Innonimate Osteotomy in the Treatment of Congenital Dislocation and Subluxation of the Hip, Aug. 1961, The Journal of Bone and Joint Surgery, vol. 43B No. 3, P518–539.*

Canale, S. et al., "Innominate Osteotomy in Legg–CalvePerthes Disease", *TheJournal of Bone And Joint Surgery*, vol. 54–A, No. 1, pp. 25–40 (Jan. 1972).

Maxted, M. et al., "Innominate Osteotomy In Perthes' Disease", *The Journal Of Bone And Joint Surgery*, vol. 67–B, No.3, 3 pgs (May 1985).

Millis, M. et al., "Transiliac Lengthening of the Lower Extremity", *The Journal Of Bone And Joint Surgery*, vol. 61–A, No. 8, pp. 1182–1194 (Dec. 1979).

Moberg, A. et al., "Results After Femoral and Innominate Osteotomy in Legg–Calvé–Perthes Disease", *Clinical Orthopaedics And Related Research*, No. 334, pp. 257–264 (Jan. 1997).

Robinson, Jr., H. et al. "Innominate Osteotomy in Perthes Disease", *Journal of Pediatric Orthopaedics*, vol. 8, No. 4, pp. 426–435 (1988).

Salter, R. et al., "Innominate Osteotomy In The Treatment Of Congenital Dislocation And Subluxation Of The HIP", *The Journal Of Bone And Joint Surgery*, vol. 43–B, No. 3, pp. 518–539 (Aug. 1961).

Salter R. et al., "Treatment by innominate osteotomy", *A.A.O.S.: Instructional Course Lectures*, Part V, pp. 309–316 (Date Unknown).

Salter, R. et al., "Current Concepts Review: The Present Status of Surgical Treatment for Legg–Perthes Disease", *The Journal Of Bone And Joint Surgery*, vol. 66–A, No. 6, pp. 961–966 (Jul. 1984).

* cited by examiner

*Primary Examiner*—Dinh X. Nguyen
*Assistant Examiner*—Will H Matthews
(74) *Attorney, Agent, or Firm*—Merchant & Gould P.C.

(57) ABSTRACT

A surgical method to treat hip diseases, including Legg-Calve-Perthes disease or developmental hip dysplasia is provided. This method includes several surgical techniques: a transverse osteotomy of the posterior portion of supraacetabular portion, an oblique and inclined osteotomy of the anterior portion of the supraacetabulum, detachment of a bone block from iliac crest, anterolateral displacement of the distal fragment, and insertion of the bone block into the distracted space of the osteotomy site.

13 Claims, 4 Drawing Sheets

INNOMINATE OSTEOTOMY

BACKGROUND OF THE INVENTION

A. Field of the Invention

The invention relates to a surgical method of treating hip diseases. More specifically, the invention provides an innominate osteotomy for treating diseases such as Legg-Calve-Perthes Disease, developmental hip dysplasia, or hip dislocation.

B. Description of the Prior Art

Legg-Calve-Perthes disease is a self-limiting hip disorder caused by a varying degree of ischemia and subsequent necrosis of the femoral head. Signs of the disorder include avascular necrosis of the proximal femoral epiphysis nucleus, abnormal growth of the physis, and eventual remodeling of regenerated bone. Typically, avascular necrosis of the femoral epiphysis results in delayed occific nucleus. Articular cartilage is nourished by synovial fluid and continues to grow. Consequently, cartilage columns become distorted with some loss of cellular components and do not undergo normal ossification. This results in an excess of calcified cartilage in the primary trabecular bone. Symptoms occur with subchondral collapse and fracture.

The incidence of Legg-Calve-Perthes disease is generally greater in males than females with a male to female ratio of 4–5 to 1. Generally, Legg-Calve-Pertes disease is found in young boys (4 to 8 years old) with delayed skeletal maturity. The age at which treatment is initiated appears to be the key to a good prognosis. If detected and treated after 8 years of age, the prognosis tends to be poor.

Developmental hip dysplasia involves displacement of the femoral head from the acetabulum, which disrupts the normal development of the hip joint. Developmental hip dysplasia is estimated to occur in 1–1.5 cases per 1000 live births and includes a wide spectrum of abnormalities ranging from simple hip instability with capsula laxity to complete displacement of the femoral head from an anomalous acetabular socket. Thus, the term dysplasia includes a developmental abnormality of the hip joint in which the capsule, the proximal femur, and/or the acetabulum are defective.

Innominate osteotomy has been used to treat Legg-Calve-Perthes disease and developmental dysplasia of the hip. A widely used procedure was developed in 1961 by Robert Salter and is called a Salter osteotomy or Salter's innominate osteotomy. The objective of Salter's innominate osteotomy is to derotate the maldirected acetabulum and correct excessive acetabular antetorsion. Stability is thus improved by providing anatomic coverage of the femoral head by anterior and superolateral portions of the acetabulum in the weight bearing position.

Although successful in many cases, the Salter technique has many complications, such as loss of fixation with displacement of the distal fragment, stiffness, and loss of hip flexion. Also the patient generally requires two operations, one to perform the osteotomy and a second to remove the metal pins or screws.

SUMMARY OF THE INVENTION

The present invention provides a surgical method of treating hip diseases, including Legg-Calve-Perthes Disease, developmental hip dysplasia, and/or hip dislocation. The method includes a series of surgical procedures including a transverse osteotomy of the posterior portion of supraacetabular portion, an oblique and inclined osteotomy of the anterior portion of the supraacetabulum, detachment of a bone graft from iliac crest, anterolateral displacement of a distal section of the ilium, and insertion of the bone graft into the exposed opening of the osteotomy site.

The procedure rotates the distal section of the osteotomy site laterally and anteriorly, increasing coverage of the acetabulum over the femoral head. The procedure also establishes better concentric reduction in hips with dysplasia or dislocation. It also increases coverage of the acetabulum over the femoral head in hips with Legg-Calve-Perthes diseases to achieve better stability and remodeling of the femoral head. Additionally, the technique reduces complications by providing stability without the use of metal pins or screws. Furthermore, a patient can undergo rehabilitation earlier than with a Salter osteotomy, in part because a secondary operation is not necessary.

DETAILED DESCRIPTION OF THE INVENTION

The invention provides a surgical method of treating a hip disease, including Legg-Calve-Perthes Disease, developmental hip dysplasia, and/or hip dislocation. This method includes a series of surgical procedures including a transverse osteotomy of the posterior portion of supraacetabular portion, an oblique and inclined osteotomy of the anterior portion of the supraacetabulum, detachment of a bone graft from iliac crest, anterolateral displacement of the distal fragment, and insertion of the bone graft into the opening defined by the osteotomy site.

A. The Pelvis

To provide a better understanding of the method of the invention, a brief overview of the anatomy of the pelvis and the lower limb will be provided.

Figure 1:
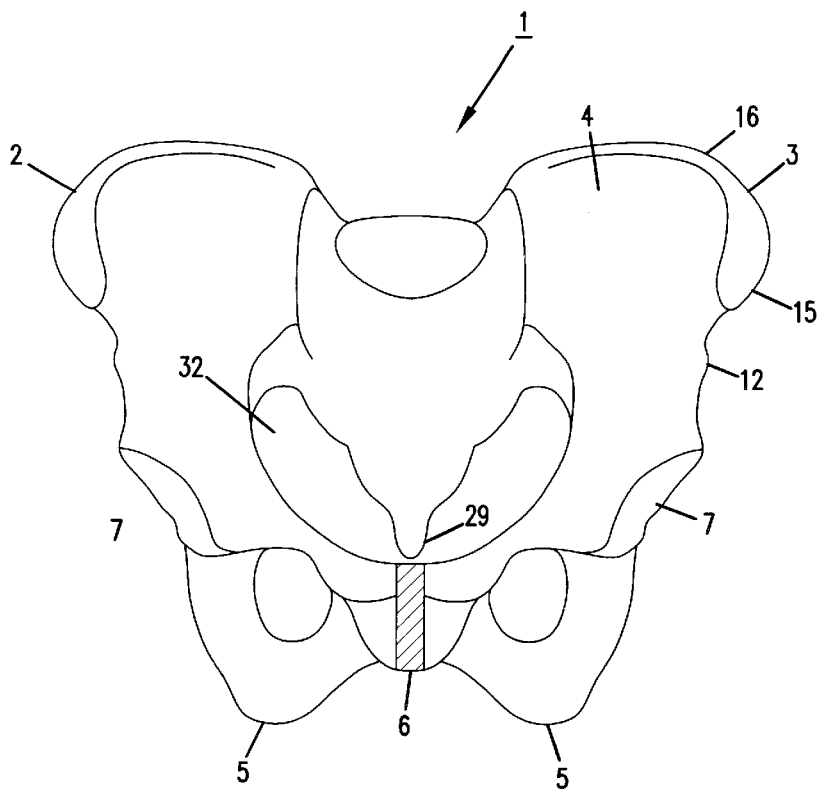
FIG. 1 is a schematic diagram of an anterior view of a pelvis.
Figure 2:
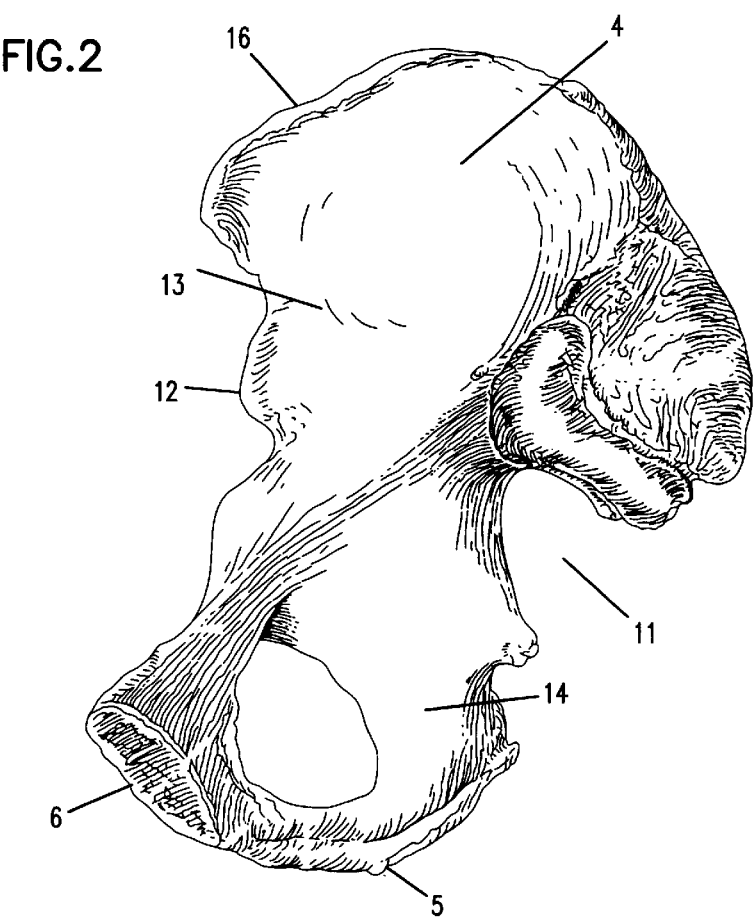
FIG. 2 is a schematic of a medial aspect of a right hip bone.
Figure 5:
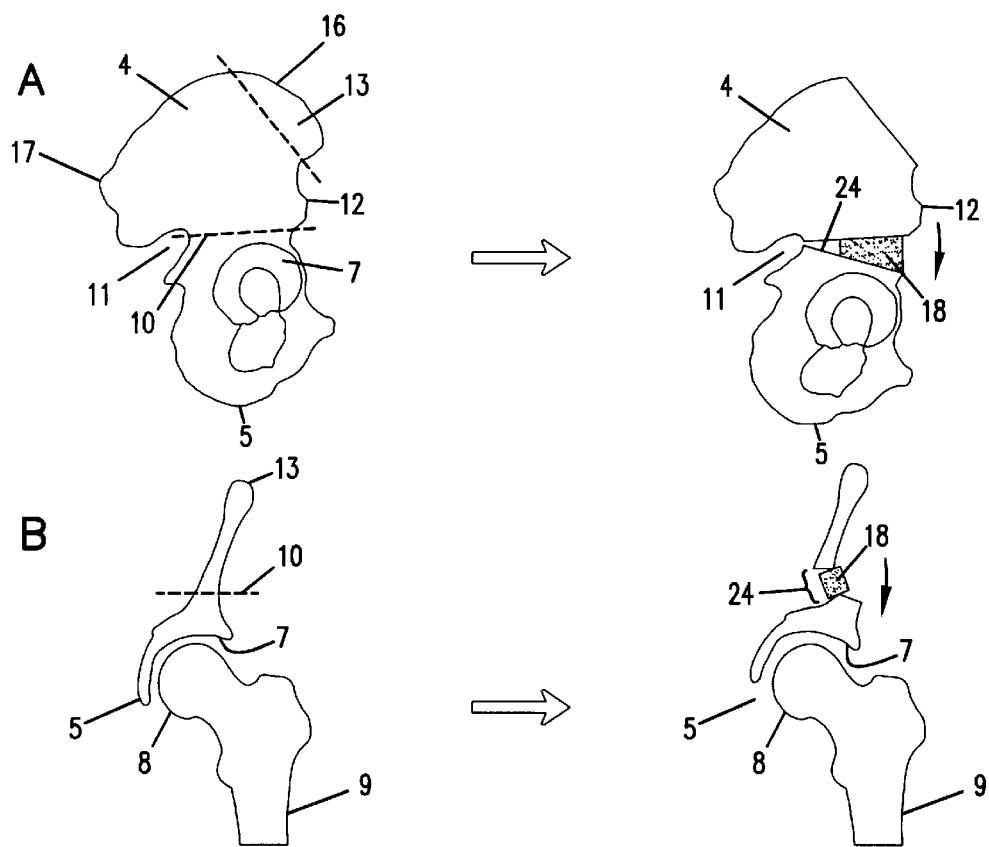
FIG. 5 is a schematic diagram illustrating the change in pelvic shape after conventional innominate osteotomy.

FIG. 1 shows an anterior view of a pelvis 1. The pelvis is formed anteriorly and laterally by a right 2 and left 3 hip bone. The right 2 and left 3 hip bones are essentially symmetrical and will not be discussed separately. The hip bones 2, 3 have three main parts: the ilium 4, ischium 5 and pubis 6. These three parts meet at the acetabulum 7, the cup shaped cavity in the lateral surface of the hip bone into which the head 8 of the femur 9 fits (See FIG. 5).

As used herein, the term "proximal section 13" of the hip bone 2, 3 refers to the section of the hip bone 2, 3 that includes the ilium 4, iliac crest 16, anterior superior iliac spine 15, posterior superior iliac spine 17, and the anterior inferior iliac spine 12, among others. The term "distal section 14" of the hip bone 2, 3 refers to the section of the hip bone 2, 3 that includes the acetabulum 7 and the ischium 5, among others.

B. Conventional Osteotomy

Figure 3:
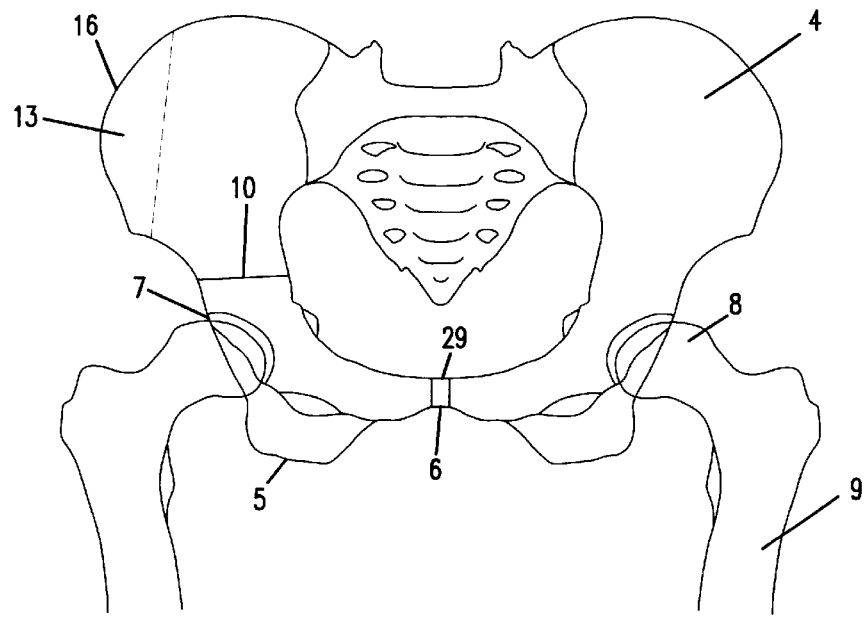
FIG. 3 is a schematic diagram illustrating a line of osteotomy in the conventional method of innominate osteotomy, drawn in relation to a whole pelvis.
Figure 4:
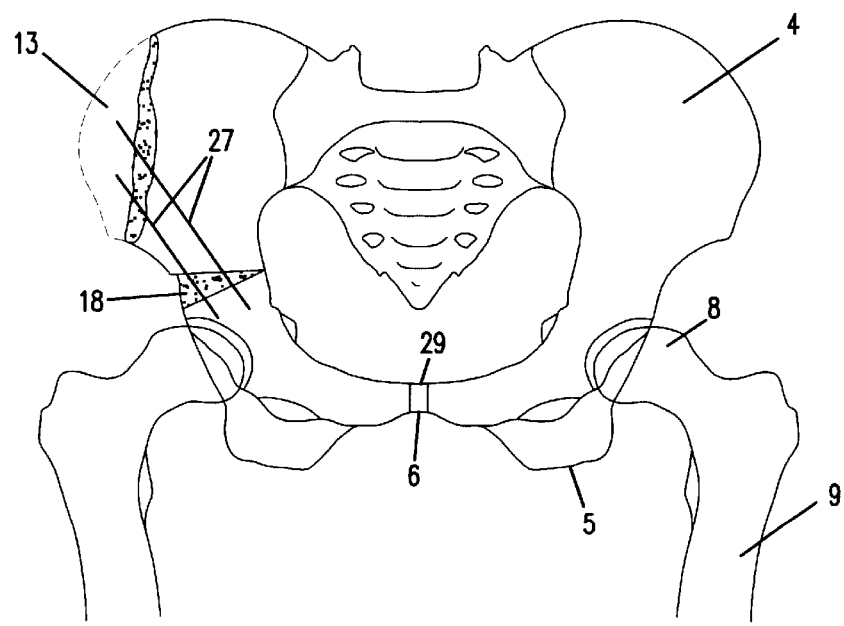
FIG. 4 is a schematic diagram illustrating a conventional innominate osteotomy in which a triangular bone fragment is inserted and fixed with two K-wires.

Again, to provide a better understanding of the method of the invention, a brief overview of Salters innominate osteotomy will be provided. As shown in FIG. 3, Salters osteotomy is performed by making a transverse linear cut 10 at a location above the acetabulum 7, at the level of the greater sciatic notch 11 and the anterior inferior iliac spine 12. After the transverse linear cut 10 is made, the distal section 14, including the acetabulum 7, is tilted inferiorly, anteriorly and laterally by rotating the distal section 14 around a pivot point at the flexible pubic symphysis 29. The rotated position of the distal section 14 is maintained by inserting a bone graft fragment 18 (typically triangular in shape), taken from the anterosuperior portion of ilium 13 (near the iliac crest 16 and/or the anterior superior iliac spine 28), into the opening 24 defined by the transverse linear cut 10.

The bone graft 18 is typically secured to the proximal 13 and distal 14 sections by two Kirshner wires 27 that traverse the proximal 13 section, the graft 18, and the distal section 14.

The femoral head 8 is thus covered by the hip 2, 3 in normal weight-bearing positions due to the rotation and redirection of the acetabulum 7.

C. The method of the Invention

According to the method of the invention, a transverse cut 20 is made starting at a medial surface 30 of the supraacetabular ilium 19, extending towards the lateral surface 31 of the supraacetabular ilium 19. Importantly, the transverse cut 20 does not extend all the way to the lateral surface 31 of the supraacetabular ilium 19 (i.e., the transverse cut extends only through a "posterior section" 21 of the supraacetabular ilium 19). As used herein, the term "medial surface" 30 refers to the surface of the ilium 4 that is proximal to the superior pelvic aperture 32. The term "lateral surface" 31 refers to the surface of the ilium 4 that is distal to the superior pelvic aperture 32. "The supraacetabular ilium 19" refers to the hip bone 2, 3 at a location superior to the acetabulum 7, and at or inferior to the greater sciatic notch 11 and/or the anterior inferior iliac spine 12. According to the invention, the transverse cut 20 preferably extends from a first location 25 at medial aspect 30 of the supraacetabular ilium 19 and terminates at a second location 26 between the medial 30 and lateral 31 surface of the ilium 4. Preferably, the transverse cut 20 terminates prior to reaching the midpoint between the medial 30 and lateral 31 surface (i.e., the transverse cut extends up to half way between the medial 30 and lateral 31 surfaces of the supraacetabular ilium 19). The transverse cut 20 can be made using any known method, for example, using a Gigli saw or a reciprocal saw.

Figure 6:
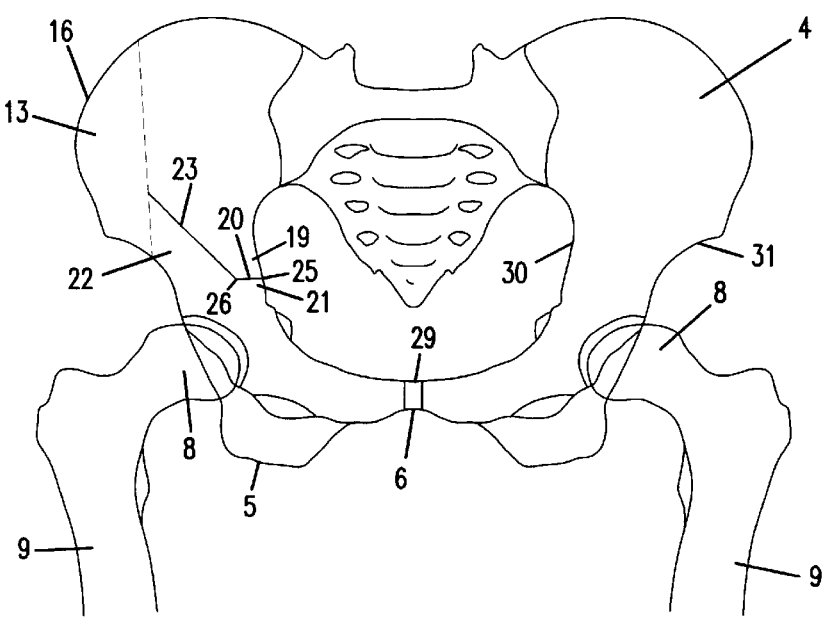
FIG. 6 is a schematic diagram illustrating the line of osteotomy in the method of the invention, drawn in relation with a whole pelvis.
Figure 7:
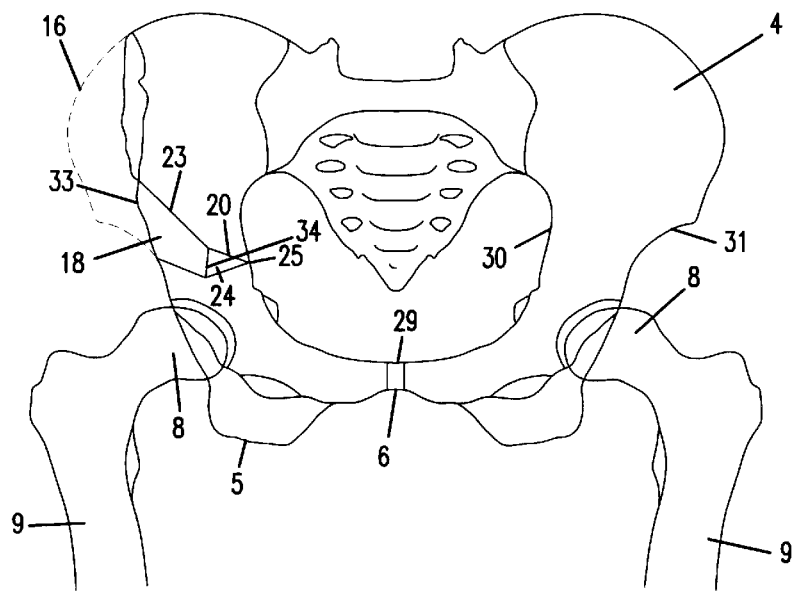
FIG. 7 is a schematic diagram illustrating the final shape of the pelvis after the method of the invention in which a triangular bone fragment is inserted and stabilized without fixation using K-wires.
Figure 8:
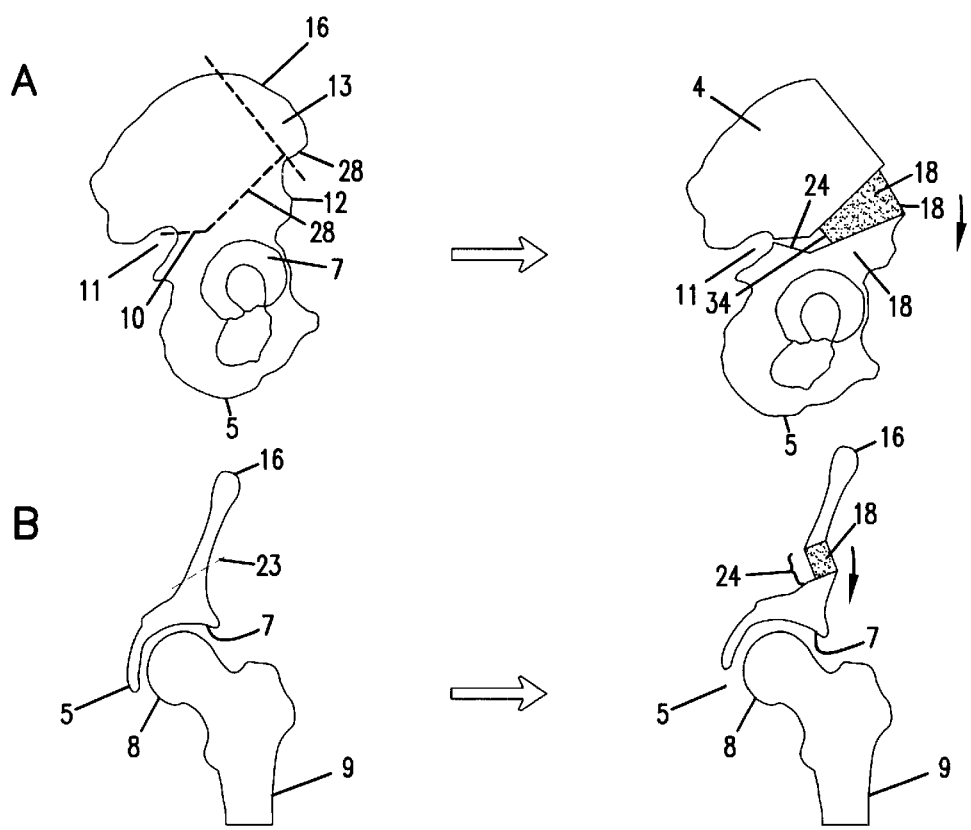
FIG. 8 is a schematic diagram illustrating the change of the shape of the pelvis after the method of the invention.

According to the invention, an oblique cut 23 is then made that extends from the transverse cut 20 towards the anterior superior iliac spine 28. Generally, the oblique cut 23 extends at an oblique angle on the coronal plane from a location near or at the second location 26 (i.e., the termination point of the transverse cut 20) with an inclined direction posteroinferiorly on the sagittal plane as shown in FIGS. 6, 7, and 8. The oblique cut 23 can be made using any known method, for example, using a Gigli saw or a reciprocal saw.

The opening 24 defined by the transverse cut 20 and the oblique cut 23 is then enlarged, for example, using a distractor and stout towel forceps. A bone graft 18, again taken from the proximal section 13 (typically the iliac crest 16 and/or the anterior superior iliac spine 28) of the ilium 4, is inserted into the opening 24. Preferably, the bone graft 18 is substantially in the shape of a wedge or a truncated wedge having one end (the major end 33) that is generally larger than the other end (the minor end 34). For example, the bone graft 18 may be substantially triangular or trapezoidal in shape. The bone graft 18 is inserted into the opening 24 defined by the transverse cut 20 and the oblique cut 23 such that the major end 33 is positioned proximal the lateral surface 31 of the ilium 4 and the minor end 34 is positioned proximal the medial surface 30 of the ilium 4 (see FIGS. 7 and 8).

At least one additional fastening member, such as wires, pins, screws, staples, etc. can be used to secure the bone graft 18 in place. Preferably a biodegradable fastening member, for example, a biodegradable screw, is used. However, such fastening members are typically not necessary. The bone graft 18 is generally stable, without the use of additional fastening members. In this new technique, the site and direction of the osteotomy is different than in prior methods. By changing the direction of the osteotomy (i.e., the transverse and oblique cuts), the method of the invention provides increased stability, even without fixation with pins, wires, screws or staples because the oblique cut 23 supports the bone graft 18 (as shown in FIG. 6).

Postoperatively, a double splint (anterior and posterior) extending from above pelvis to distal thigh is applied. During postoperative hospitalization the surgical wound is treated with temporary removal of the splint and intermittent active and assisted mobilization of the hip joint. The double splint is kept in place for 6 weeks. After 6 weeks, the patient is allowed to walk with using crutches (partial weight bearing) until radiographic bony union is observed. Then tolerable weight bearing is permitted depending on the patient's condition.

The present method also reduces the incidence of complications, such as loss of fixation with displacement of the distal fragment, stiffness, and loss of hip flexion, typically seen in conventional procedures. Patients do not have to be immobilized with hip spica cast, as in conventional procedures, to prevent loss of fixation and displacement of the distal fragment. Additionally, the present technique is easy to perform and generally requires less operation time.

EXAMPLE

A patient is placed on an operating table in a semilateral decubitus position or supine position. The patient's lower limb is prepared and draped to allow free motion of the hip during operation. Prior to the osteotomy, an adductor tenotomy may be performed if the tendon is tight. Generally, an incision is made starting from the middle of the iliac crest, extending anteriorly along the iliac crest, and finishing around midpoint of the inguinal ligament. The subcutaneous tissue is divided in line with the skin incision. The fascia lata is incised along the medial border of the tensor fascia lata. The cartilaginous iliac apophysis under the incised skin is split in the middle down to the bone. The periosteum is elevated in both sides of the ilium to expose the sciatic notch. The iliopsoas tenotomy is performed.

A transverse cut is made through the posterior section of the supraacetabular ilium using a Gigli saw. An oblique cut is then made using a reciprocal saw. The opening defined by the transverse cut and the oblique cut is then enlarged using a distractor and stout towel forceps. Distraction may be easily performed if the leg is extended and externally rotated with traction of the leg by an assistant. A triangular bone graft taken from the iliac crest is inserted into the opening.

The two halves of the cartilaginous iliac apophysis are sutured together over the iliac crest. The wound is closed using routine techniques.

Postoperatively, a double splint (anterior and posterior) extending from above pelvis to distal thigh is applied. During postoperative hospitalization the surgical wound is treated with temporary removal of the splint and intermittent active and assisted mobilization of the hip joint. The double splint is kept in place for 6 weeks. After 6 weeks, the patient is allowed to walk with using crutches (partial weight bearing) until radiographic bony union is observed. Then tolerable weight bearing is permitted depending on the patients condition.

What is claimed is:

1. A method of treating a disease of a hip, said hip comprising an ilium having a proximal section and a distal section, an iliac crest, and a subpraacetabular ilium having a medial and a lateral surface, comprising:

surgically accessing the hip;

making a transverse cut that extends from a first location at the medial surface of the supraacetabular ilium to a second location up to halfway between the medial surface and the lateral surface the supraacetabular ilium;

making an oblique cut extending from the transverse cut towards the iliac crest, such that the oblique cut and the transverse cut define an opening between the proximal section and the distal section;

rotating the distal section of the hip anteriorly, laterally and inferiorly;

obtaining a bone graft;

enlarging the opening defined by the transverse cut and the oblique cut;

inserting the bone graft into the opening defined by the transverse cut and the oblique cut; and surgically closing access to the hip.

2. The method of claim 1, wherein the step of obtaining the bone graft comprises surgically detaching a bone graft from the proximal section of the ilium.

3. The method of claim 1, wherein the hip diseases is selected from the group consisting of Legg-Calve-Perthes disease, developmental hip dysplasia, and hip dislocation.

4. The method of claim 1, further comprising a step of securing the bone graft to the proximal and distal section of the ilium with at least one fastening member.

5. The method of claim 4, wherein the fastening member is biodegradable.

6. The method of claim 4, wherein the fastening member is selected from the group consisting of a screw, pin, staple and wire.

7. The method of claim 1, wherein the oblique cut extends in an oblique direction on a coronal plane with an inclined direction posterioinferiorly on a saggital plane.

8. The method of claim 1, wherein the oblique cut extends from the second location between the medial surface and the lateral surface the supraacetabular ilium.

9. The method of claim 1, wherein the step of making a transverse cut comprises making a cut with a Gigli saw or a reciprocal saw.

10. The method of claim 1, wherein the step of making an oblique cut comprises making a cut with a Gigli saw or a reciprocal saw.

11. The method of claim 1, wherein the bone graft is surgically detached from the iliac crest.

12. The method of claim 1, wherein the bone graft is substantially shaped like a wedge or a truncated wedge.

13. The method of claim 12, wherein the bone graft is triangular or trapezoidal in shape.

* * * * *